United States Patent
LaLonde

(10) Patent No.: US 8,298,219 B2
(45) Date of Patent: Oct. 30, 2012

(54) CRYOTREATMENT DEVICE USING A SUPERCRITICAL GAS

(75) Inventor: Jean-Pierre LaLonde, Québec (CA)

(73) Assignee: Medtronic Cryocath LP, Toronto, Ontario (CA)

(*) Notice: Subject to any disclaimer, the term of this patent is extended or adjusted under 35 U.S.C. 154(b) by 537 days.

(21) Appl. No.: 12/552,399

(22) Filed: Sep. 2, 2009

(65) Prior Publication Data
US 2011/0054453 A1 Mar. 3, 2011

(51) Int. Cl.
*A61B 18/02* (2006.01)
(52) U.S. Cl. .......................... 606/21; 606/22
(58) Field of Classification Search ............... 606/20–26
See application file for complete search history.

(56) References Cited

U.S. PATENT DOCUMENTS

| | | | |
|---|---|---|---|
| 6,575,966 B2 * | 6/2003 | Lane et al. | 606/21 |
| 6,592,577 B2 * | 7/2003 | Abboud et al. | 606/22 |
| 7,083,612 B2 * | 8/2006 | Littrup et al. | 606/21 |
| 7,273,479 B2 * | 9/2007 | Littrup et al. | 606/21 |
| 7,310,955 B2 * | 12/2007 | Hume et al. | 62/52.1 |
| 2008/0173028 A1 | 7/2008 | Littrup et al. | |
| 2010/0057067 A1 | 3/2010 | Baust et al. | |
| 2011/0054453 A1 * | 3/2011 | LaLonde | 606/23 |

FOREIGN PATENT DOCUMENTS
CA 2378054 A1 4/2001

OTHER PUBLICATIONS
Supercritical Fluid, Wikipedia, Jan. 20, 2010, http://en.wikipedia.org/wiki/Supercritical_fluid.

* cited by examiner

*Primary Examiner* — Michael Peffley
(74) *Attorney, Agent, or Firm* — Christopher & Weisberg, P.A.

(57) ABSTRACT

A method of cryogenically treating a tissue region is provided, including positioning a treatment region of a medical device proximate the tissue region; transferring coolant in a substantially liquid phase from a coolant reservoir to a subcooler; transitioning the coolant from the liquid phase into a supercritical state; transferring the supercritical coolant to the treatment region; changing the coolant from the supercritical state to at least one of a liquid phase and a gaseous phase at the treatment region; ablating the tissue region; and evacuating coolant from the treatment region of the medical device.

15 Claims, 8 Drawing Sheets

CRYOTREATMENT DEVICE USING A SUPERCRITICAL GAS

CROSS-REFERENCE TO RELATED APPLICATION n/a

STATEMENT REGARDING FEDERALLY SPONSORED RESEARCH OR DEVELOPMENT n/a

FIELD OF THE INVENTION

The present invention relates to a coolant system and method of use for a cryogenic medical device.

BACKGROUND OF THE INVENTION

A number of cooled catheter systems have been developed for treating tissue in a cardiac setting, either to cool the tissue sufficiently to stun it and allow cold mapping of the heart and/or confirmation of catheter position with respect to localized tissue lesions, or to apply a more severe level of cold to ablate tissue at the site of the catheter ending. In general, the range of treatments which may be effected by a cryocatheter is comparable to the range of applications for radio frequency or thermal ablation catheters, and in particular, these instruments may be configured to achieve either small localized ball shape lesions at the tip of the catheter, or one or more elongated linear lesions extending a length of several centimeters or more along the tip. The latter form of lesion is commonly used to achieve conduction block across a region of the cardiac wall so as to sever an aberrant pathway over a length, preventing conduction across the region, in order change the cardiac signal path topology, for example, to eliminate a faulty pathway responsible for atrial fibrillation or a tachycardia.

A cryogenic device uses the energy transfer derived from thermodynamic changes occurring in the flow of a refrigerant through the device. Various fluids with low operating temperatures (such as cryogens or cryogenic refrigerants) have been used in the medical and surgical field to treat such tissue aberrations. In general, a cryogenic device uses the energy transfer derived from thermodynamic changes occurring in the flow of a cryogen therethrough to create a net transfer of heat flow from the target tissue to the device, typically achieved by cooling a portion of the device to very low temperature through conductive and convective heat transfer between the cryogen and target tissue. The quality and magnitude of heat transfer is regulated by the device configuration and control of the cryogen flow regime within the device.

Structurally, cooling can be achieved through injection of high pressure refrigerant through an orifice. Upon injection from the orifice, the refrigerant undergoes two primary thermodynamic changes: (i) expanding to low pressure and temperature through positive Joule-Thomson throttling, and (ii) undergoing a phase change from liquid to vapor, thereby absorbing heat of vaporization. The resultant flow of low temperature refrigerant through the device acts to absorb heat from the target tissue and thereby cool the tissue to the desired temperature.

A number of different fluids have been used for the coolant component of cryotreatment catheters, such as a concentrated saline solution or other liquid providing some degree of thermal conductivity and heat capacity. However, typical refrigerants and their respective refrigeration systems may be limited in their thermal conductivity and/or capacity to remove heat, either because of their particular thermal properties or because of insufficient temperature reduction prior to delivery of the refrigerant to a catheter.

To some extent these considerations have been addressed by using a phase change material as the cryogenic fluid, and arranging the catheter such that the phase change, e.g., from a liquid to a gas, occurs in the treatment portion of the catheter tip. Another possible approach is to employ a pressurized gas, and configure the catheter for cooling by expansion of the gas in the tip structure. However, owing to the small size that such a catheter is required to assume for vascular insertion, or the awkwardness of handling a cryogenic treatment probe generally, the design of a safe and effective coolant circulation system which nonetheless dependably provides sufficient cooling capacity at a remote tip and minimizes treatment times while increasing ablative lesion depth and quality remains a difficult goal.

Accordingly, it is desirable to provide a coolant system consistently, controllably delivering coolant to a treatment device with a cooling capacity that minimizes treatment time and improves the depth and quality of treatment.

SUMMARY OF THE INVENTION

The present invention advantageously provides a method and system for delivering coolant to a medical device and thermally treating a tissue region. In particular, a method of delivering coolant to a medical device is provided, including transferring a coolant in a supercritical state to a treatment region of the medical device; and changing the coolant from the supercritical state to at least one of a liquid phase and a gaseous phase at the treatment region. The method may include changing the coolant from the supercritical state to at least one of a liquid phase and a gaseous phase involving ejecting the coolant from a Joule-Thompson valve. The coolant may be changed from a supercritical state into a mixed liquid-gaseous state, and. transferring the coolant in a supercritical state to a treatment region of the medical device can include subcooling the coolant. The method may include drawing coolant from a reservoir in a liquid phase, and transitioning the coolant into a supercritical phase for delivery to the medical device, where transitioning the coolant into a supercritical phase for delivery to the medical device includes raising the pressure of the coolant with a pressure regulator. The method may also include monitoring a pressure level within the medical device and evacuating coolant from the medical device when the monitored pressure level varies from a predetermined target pressure.

A method of cryogenically treating a tissue region is also provided, including positioning a treatment region of a medical device proximate the tissue region; transferring coolant in a substantially liquid phase from a coolant reservoir to a subcooler; transitioning the coolant from the liquid phase into a supercritical state; transferring the supercritical coolant to the treatment region; changing the coolant from the supercritical state to at least one of a liquid phase and a gaseous phase at the treatment region; ablating the tissue region; and evacuating coolant from the treatment region of the medical device.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION OF THE INVENTION

Figure 1:
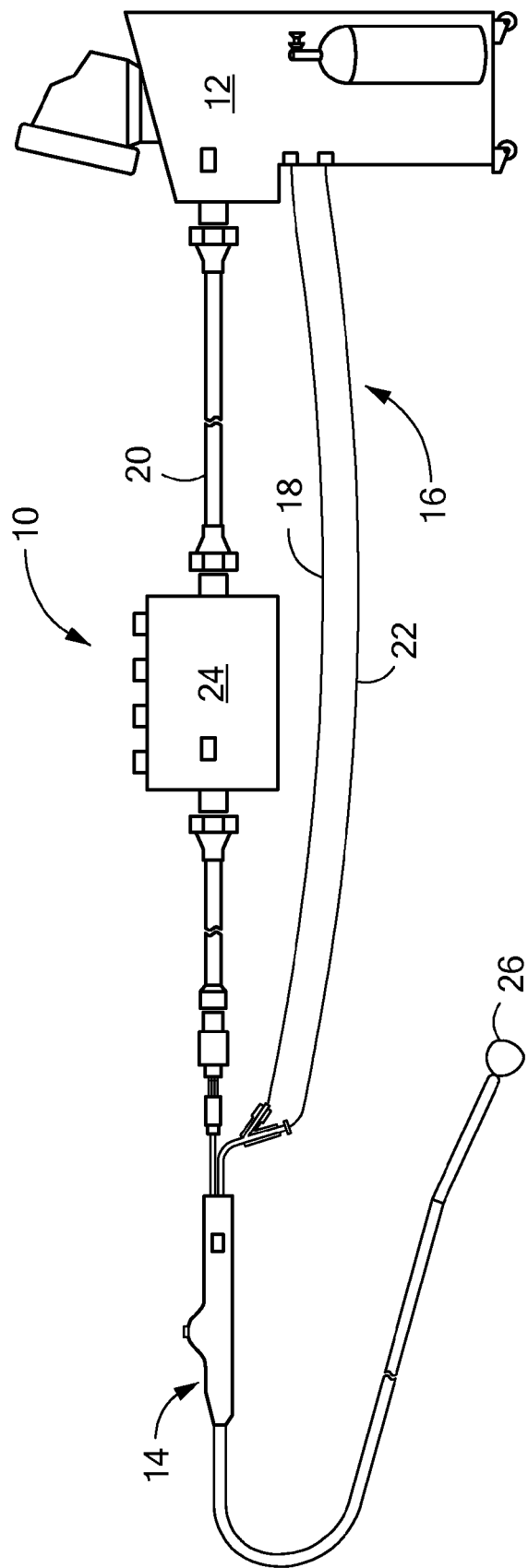
FIG. 1 illustrates an embodiment of a medical system constructed in accordance with the principles of the present invention.

The present invention includes a cryogenic cooling system and a medical device for use therewith. Referring now to the drawing figures in which like reference designations refer to like elements, an embodiment of a medical system constructed in accordance with principles of the present invention is shown in FIG. 1 and generally designated as "10." The system generally includes a cooling unit or console 12 coupled to a medical device 14 through an umbilical system 16. The medical device 14 may be a medical probe, a catheter, a balloon-catheter, as well as other devices deliverable or otherwise positionable through the vasculature and/or proximate to a tissue region for treatment. In particular, the medical device 14 may include a device operable to thermally treat a selected tissue site, including cardiac tissue.

Umbilical system 16 may include three separate umbilicals: a coaxial cable umbilical 18, an electrical umbilical 20 and a vacuum umbilical 22. An outer vacuum umbilical may be suitable for a medical device having multiple layers or balloons. If the user wishes to perform a radiofrequency ("RF") ablation procedure, radiofrequency energy can be provided to electrodes on the medical device 14 via electrical umbilical 20 to perform an RF ablation technique. Electrical umbilical 20 can include an electrocardiograph ("ECG") box 24 to facilitate a connection from electrodes on medical device 14 to an ECG monitor (not shown). Coaxial umbilical 18 may include both a cooling injection umbilical and a vacuum umbilical that provide respective inlet and return paths for a refrigerant or coolant used to cool a tissue-treating section of the device 14. The vacuum umbilical 22 may provide a safety conduit allowing excess coolant or gas to escape from the device 14 if the pressure within the medical device 14 exceeds a predefined limit. The vacuum umbilical 22 can also be used to capture air through a leak of the outer vacuum system where it is outside the patient and as a lumen to ingress blood when inside the patient.

Figure 2:
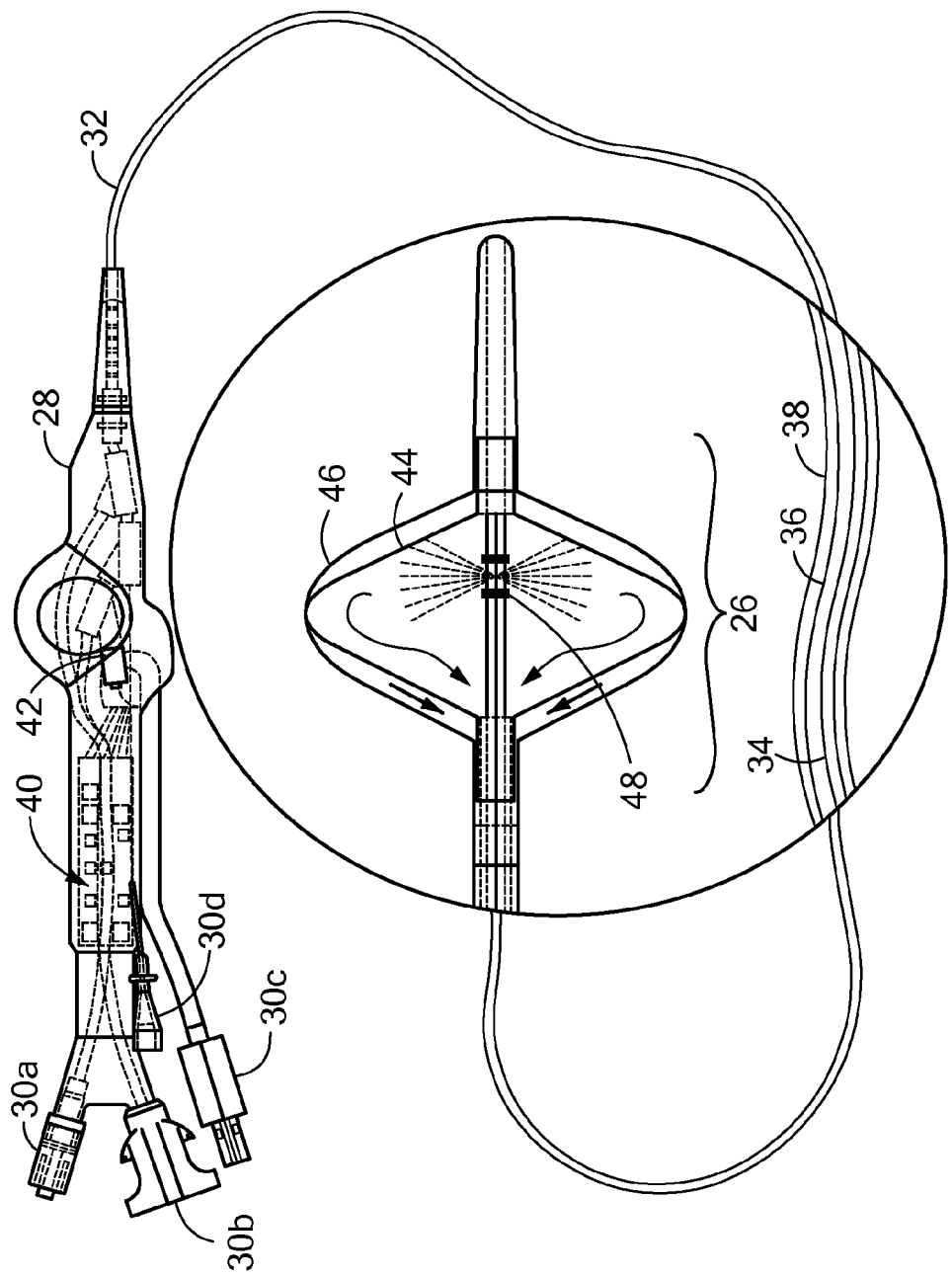
FIG. 2 illustrates an embodiment of a medical device constructed in accordance with the principles of the present invention.

Now referring to FIG. 2, the medical device 14 is shown in more detail. The medical device may include a treatment region 26 for energy interaction between the medical device 14 and a treatment site. The treatment region 26 may include, for example, a balloon structure that can be a single wall or a double wall configuration. In a double-wall or dual-balloon configuration, the space or junction between balloon walls may be in communication with a vacuum source. In particular, the medical device may include a handle 28 having a number of proximal connector ports 30a-30d. Port 30a may be a first vacuum connector, having a first vacuum lumen therein, such as a 10 French lumen. Port 30b may be a coaxial connector having both a vacuum lumen and injection therein, the vacuum lumen being a second vacuum lumen, such as an 8 French lumen. Port 30c may be an electrical connector and port 30d may be a guidewire luer hub. The medical device 14 may include an elongate, flexible catheter body 32 having a guidewire 34 and an inner shaft 36 and outer shaft 38 having one or more lumens defined therethrough for the circulation and or deliver of a fluid or coolant to the treatment region 26 of the medical device 14.

The handle 28 may include blood detection circuitry 40 and a pressure relief valve 42. The treatment region 26 of the medical device 14 may include a first, inner expandable element (such as a balloon) 44 and a second, outer expandable element 46 surrounding the first expandable element 44. Radiopaque marker bands 48 may be located proximate the exit point of coolant injected into the treatment region 26 to aid in the positioning and tracking of the device.

The medical system 10 may also include one or more sensors to monitor the operating parameters throughout the system, including for example, pressure, temperature, flow rates, volume, or the like in the console 12, the umbilical system 16, or the medical device 14.

Figure 3:
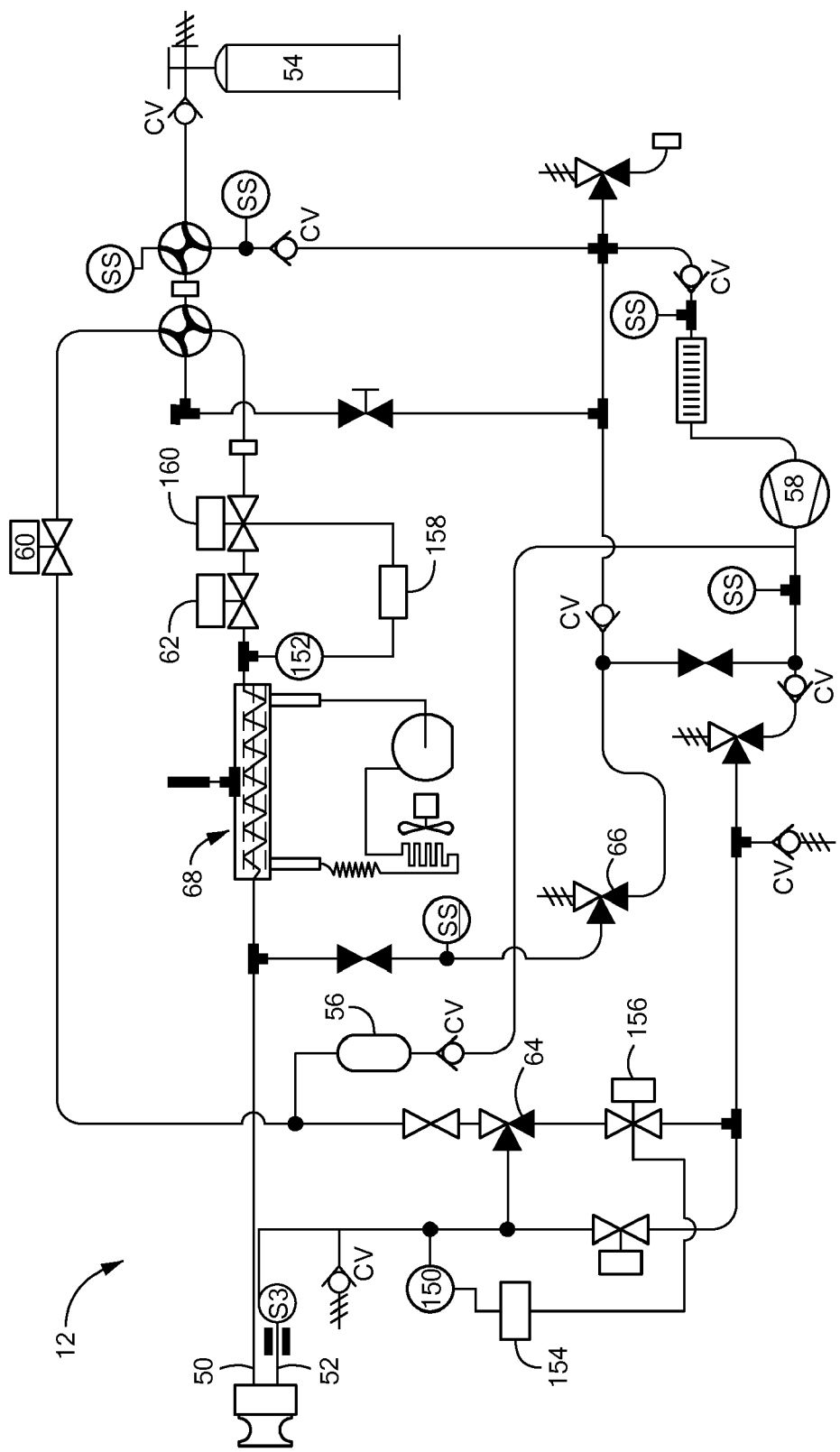
FIG. 3 is a schematic representation of an embodiment of a cooling system constructed in accordance with the principles of the present invention.

Now referring to FIG. 3, a schematic representation of the console 12 for use with a medical device is shown. The console 12 includes various mechanical and/or electrical components to assist in the operation, control, and/or monitoring of the medical device 14. Primarily, the console 12 may be coupled to the medical device 14 through the umbilical system 16 to place a fluid supply lumen 50 and an exhaust lumen 52 of the console 12 in fluid communication with the treatment region 26 of the medical device 14. In general, the console 12 may further include a first coolant reservoir 54, a second coolant reservoir 56, and a vacuum source 58 As used herein, the term 'reservoir' is intended to include any container or chamber able to contain a fluid. As such, either of the first or second reservoirs may include a tank, container, or even a length of tubing or the like defining an interior space between two or more valves. The second coolant reservoir 56 may have a volumetric capacity smaller than the volumetric capacity of the first coolant reservoir 54 (such as 20 cubic centimeters for example), which has been shown to reduce the likelihood of cardiac abnormalities and/or failure due to coolant egress into the vascular system. The vacuum source 58 may include any structure and/or apparatus able to provide a negative pressure gradient for providing fluid flow, including pumps, plunger devices, or the like.

One or more valves may be disposed about the console 12 in fluid communication with the supply lumen 50 and/or the exhaust lumen 52 for manipulating and/or providing fluid flow along a desired path. For example, the console 12 may include a pair of valves, 60 and 62, in fluid communication with the first coolant reservoir 54 such that the first coolant reservoir 54 may be selectively switched from being in fluid communication with the second coolant reservoir 56 to being in fluid communication with the supply lumen 50. Moreover, a valve 64 may be disposed on the exhaust lumen 52 such that the exhaust lumen 52 may be selectively switched from being in fluid communication with the second coolant reservoir 56 to being in fluid communication with the vacuum source 58. In addition, the console 12 may include one or more check valves and/or pressure relief valves CV configured to open to atmosphere or to a recovery tank should a pressure level and/or flow rate within a portion of the console 100 exceed a desired or predetermined level. Such valves may further be operated to open portions of the system if so desired.

The console 12 may include a valve 66 in fluid communication with both the supply lumen 50 and the exhaust lumen 52. In particular, the valve 66 may be in fluid communication with the supply lumen 50 at a position upstream of the umbilical connector, while being in fluid communication with the exhaust lumen 52 downstream from the umbilical connector. The valve 66 may further be placed in fluid communication with the surrounding atmosphere to equalize pressure in both the exhaust and supply lumens. During operation, the console 12 may detect a failure of the medical device 14, such as an indication of the presence of blood or bodily fluid being entrained into the coolant system. Upon such detection, coolant flow may be terminated. However, despite the termination of coolant flow, due to the built-up pressure levels in the supply and exhaust lumens, bodily fluid may continue to be siphoned into the medical device and thus into portions of the console 12. To reduce the likelihood that siphoning occurs, the valve 66 may be actuated to place both the supply lumen 50 and the exhaust lumen 52 into fluid communication with the atmosphere. By doing so, the pressure in either lumen will be substantially equalized and thus will prevent the further ingress of bodily fluids into the medical device and thus the console. Of course, the equalization and/or subjection of both the supply and exhaust lumens may be achieved by using one or more valves in various configuration.

The console 12 may also include a subcooler 68 disposed about a portion of the supply lumen 50 for achieving a desired temperature and/or coolant phase of fluid flowing therethrough. The subcooler 68 may include a compressor, condenser and the like placed in thermal communication with the supply lumen 50 as previously discussed.

Figures 5, 6:
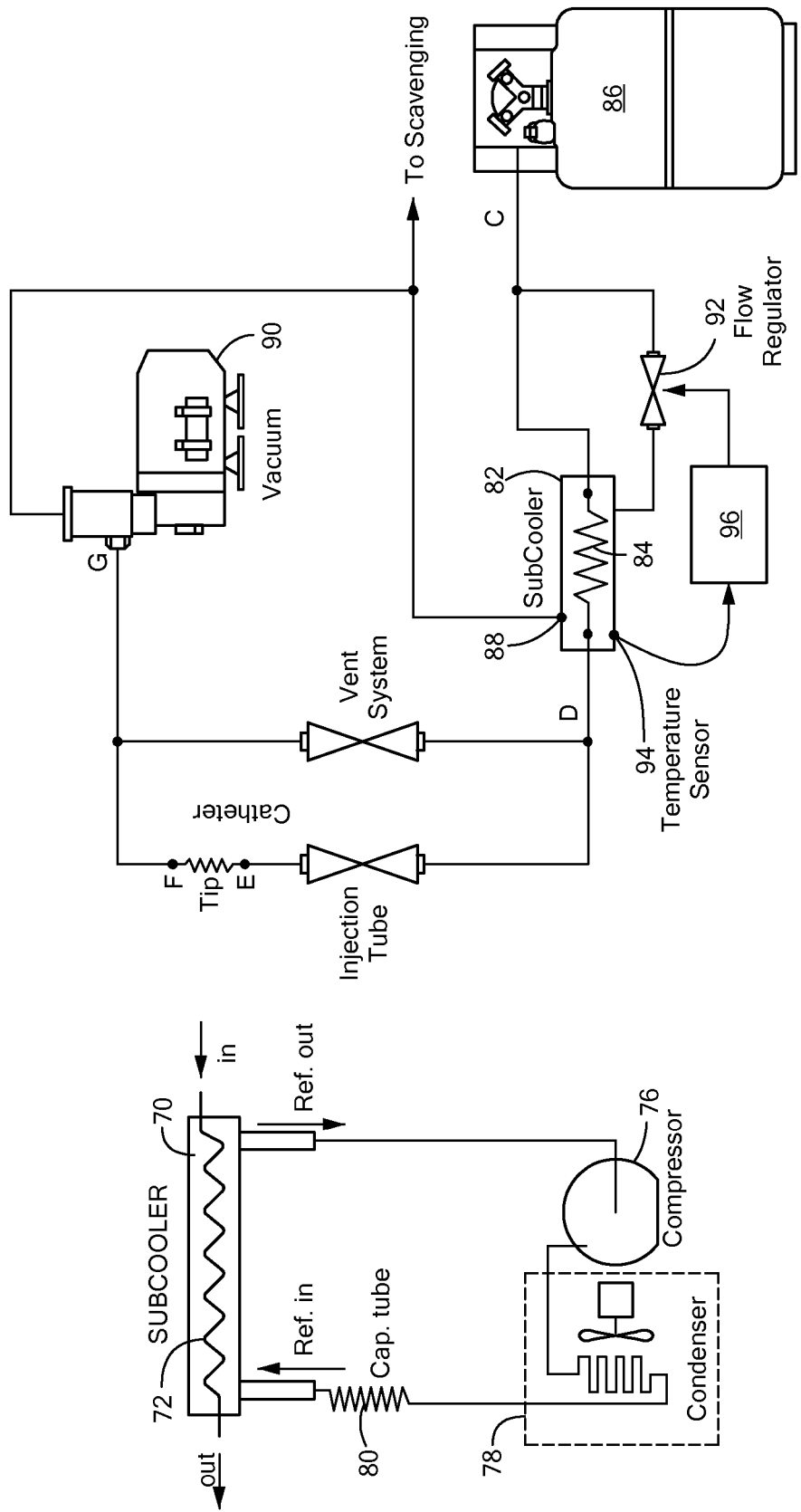
FIG. 5 schematically represents an embodiment of a subcooler for the medical system according to the present invention.
FIG. 6 schematically represents another embodiment of a subcooler for the medical system according to the present invention.

FIG. 5 discloses an example of a closed-loop subcooler in schematic form. As shown, the subcooler includes a heat exchange chamber 70 having a coiled refrigerant transfer line 72 passing therethrough. A compressor 76 and condenser 78 provide liquid refrigerant that is transferred into the chamber 70 as shown by the arrow marked "Ref. in." The coolant, if compressed gas expands, or if liquid changes state to gas, thereby chilling the transfer line 72 and its contents. The expanded, gas-state coolant is exhausted from the chamber 70 as shown by the arrow marked "Ref. out" and returned to the compressor 76; A capillary tube 80 can be interposed between the condenser 78 and the chamber 70 in order to reduce the coolant flow into the heat exchanging chamber 70.

Another example of a subcooler 68 of the present system is shown in FIG. 6. The subcooler includes an insulated enclosure 82 (like chamber 70) encloses a coiled portion of a coolant supply line 84 leading to a medical implement (not shown) as described above. The coolant supply line 84 is in communication with a coolant reservoir 86 to allow coolant to be directed into the enclosure 82. An outlet 88 in communication with a vacuum source 90 is provided to exhaust coolant from the enclosure 82 whereupon it is directed to a scavenging system. Cooling performance can be controlled with a coolant flow regulator 92 that can be made responsive to a temperature sensor 94 within the enclosure 82 that outputs a signal to a temperature controller 96 that controls the flow regulator 92.

Figure 7:
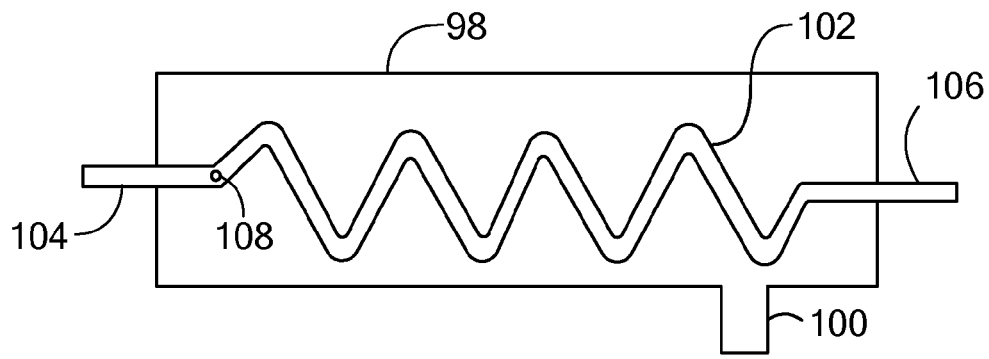
FIG. 7 schematically represents an additional embodiment of a subcooler for the medical system according to the present invention.

Referring now to FIG. 7, an alternate subcooling configuration is shown. Chamber 98 is depicted having an outlet 100. Provided within the chamber 98 is a conduit 102, having a first end 104 and a second end 106, defining a fluid flow path for a coolant or a refrigerant. The conduit 102 defines an aperture 108. In practice, a refrigerant is supplied to the first end 104 which then passes through the body of the conduit 102 to the second end 106. After the refrigerant enters the conduit 102, a portion of the refrigerant is directed into the chamber 98 via the aperture 108. The refrigerant then expands to thereby cool the chamber 98 and in turn the conduit 102. The expanded refrigerant is then evacuated from the chamber 98 via the outlet 100. The rate of flow through the aperture 108 can be controlled by the size of the aperture as well as by flow control valves as discussed herein (not shown). The diameter of the aperture can range from 0.0001 to 0.03 inches, for example. The rate of subcooling affected within the chamber 98 can be regulated by adjusting the flow rate of the outlet 100. By decreasing the flow rate allowed at the outlet 100, the amount of refrigerant entering the chamber 98 via the aperture 108 is thereby decreased and the subcooling reduced. Further, it is contemplated that the location of the aperture along the conduit 102 can be varied.

Figure 8:
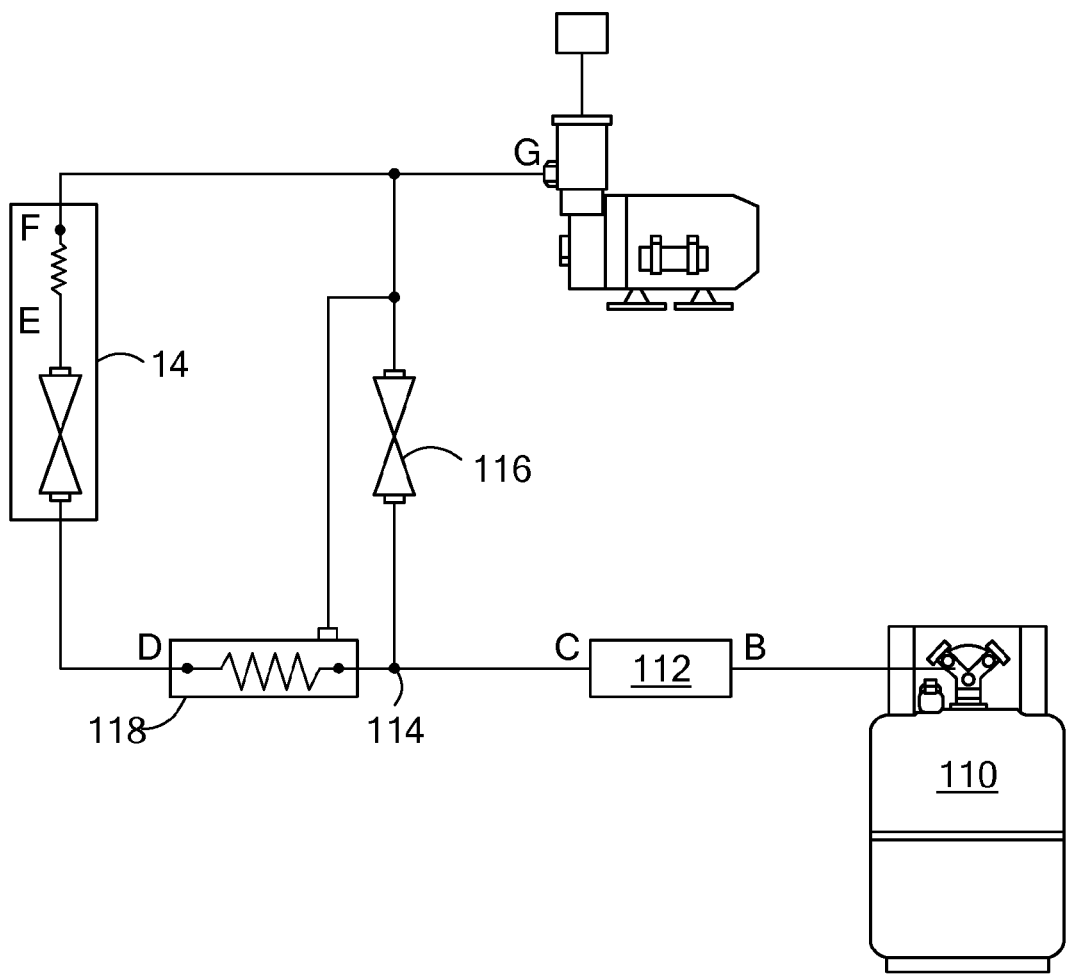
FIG. 8 schematically represents still another embodiment of a subcooler for the medical system according to the present invention.

Referring now to FIG. 8 which is a schematic view of another alternate embodiment of a subcooler illustrated in more detail. In the illustrated arrangement, refrigerant is supplied to the system from a coolant source 110. The refrigerant passes through a filter or contaminant remover 112 (optional) and then to a junction 114. One branch of the junction passes through a vent system 116 and the other branch passes through subcooler 118. The subcooler 118 chills the refrigerant to a temperature that causes the refrigerant to be in the liquid state prior to transfer to the medical device 14. The illustrated arrangement permits placement of the subcooler within accessories external to the console, for example, in an connection box or intermediary console (not shown), in a catheter handle assembly or any other such device located between the medical device 14 and the console 12.

Figure 9:
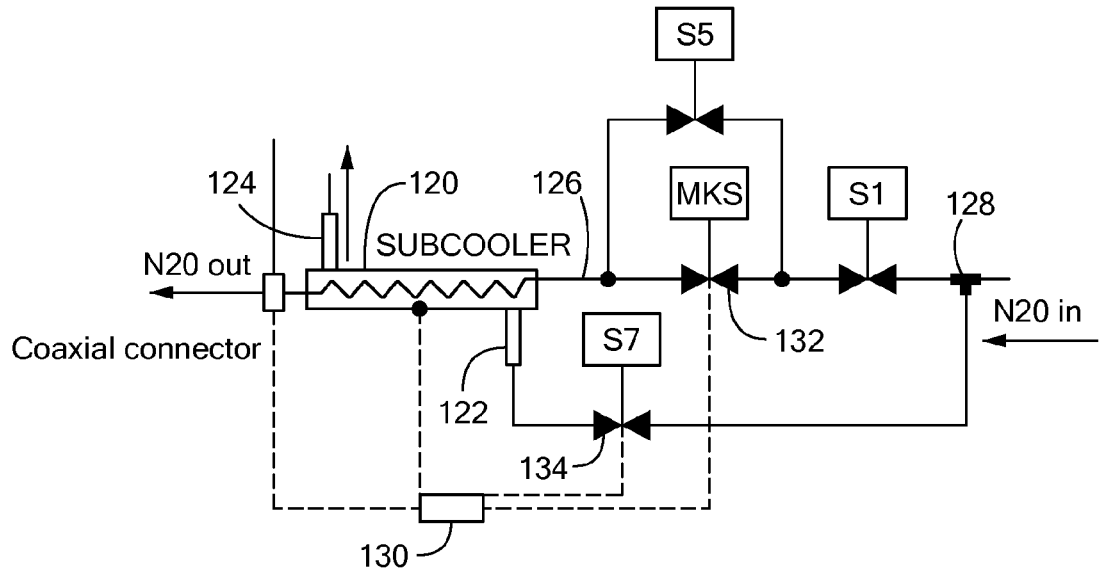
FIG. 9 schematically represents an additional embodiment of a subcooler for the medical system according to the present invention.

Referring now to FIG. 9, yet another configuration for a subcooler is illustrated in conjunction with a control system for the subcooler. As with configurations described above, this illustration depicts a heat exchange chamber 120, having an inlet 122 and an outlet 124, provides a flow path for refrigerant such as nitrous oxide or another fluid. A conduit 126 that defines a second fluid flow path for the same refrigerant passes through the chamber 120 and is in fluid communication with a refrigerant supply upstream of the chamber and a medical device downstream from the chamber. As shown, a fluid flow splitter 128 can allow a common refrigerant source to be used for supplying the chamber 120 and the conduit 126.

A programmable controller 130 is in communication with and controls one or more valves, such as a first valve 132, to regulate flow of coolant through the conduit 126 and into the medical device in response to a programmed cooling profile and in response to sensor outputs from the catheter. Additionally, the controller 130 can be used to control a second valve 134 to regulate flow of coolant through the chamber 120 in response to sensed temperature within the chamber. For example, the controller 130 can establish a duty cycle that opens and closes the second valve 134 repeatedly over time.

If the temperature rises in the chamber 120, the second valve 134 can be opened and closed more frequently. By contrast, if the temperature in the chamber falls too far, the second valve 134 can be cycled less frequently. Another example includes establishing a duty cycle to specifically regulate the temperature increases and decreases at the treatment site. It is advantageous to be able to precisely control the freezing and thawing rates of the treatment region 26 of the medical device 14 when performing a medical treatment procedure. Further, by sensing the actual temperatures and adjusting the opening and closing of the system valves, the application of specific temperature regimens can be accomplished.

Figure 10:
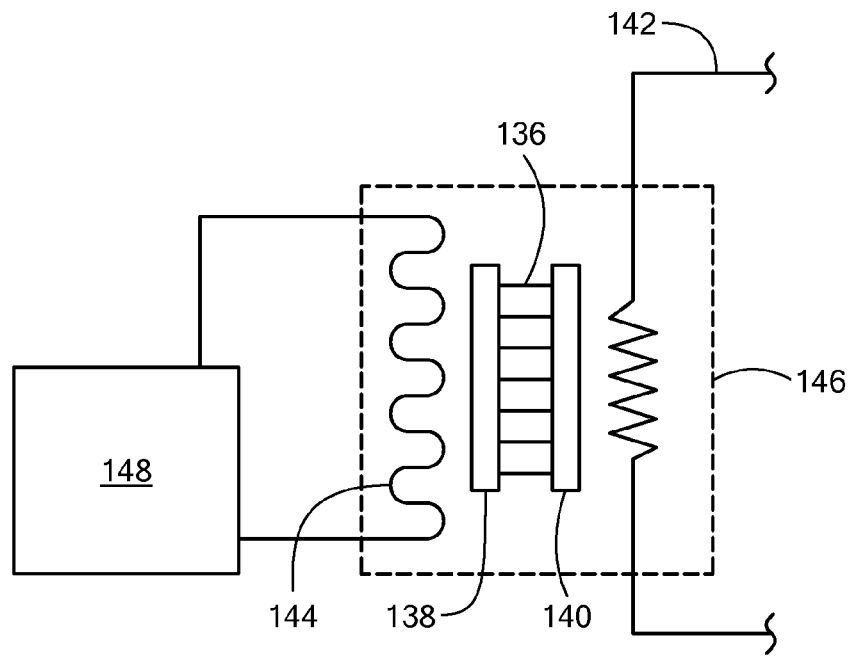
FIG. 10 schematically represents an embodiment of a subcooler for the medical system according to the present invention.

Referring now to FIG. 10, yet another configuration for a subcooler is illustrated in conjunction with a control system for the subcooler. The subcooler feature is provided by a thermoelectric cooler 136, such as a peltier cooler, the operation of which is known in the art. The thermo-electric cooler has a hot side 138 and a cold side 140. A conduit 142 is provided adjacent and in thermally-conductive communication with the cold side 140 of the thermo-electric cooler 136. A supplemental cooler 144 is provided adjacent to and in thermally-conductive communication with the hot side 138 of the thermoelectric cooler. The conduit 142, the thermoelectric cooler 136 and the supplemental cooler 144 are enclosed by a housing 146. The supplemental cooler 144 is connected to an external cooling source 148 which can be any of the cooling arrangements disclosed herein or other such devices.

When the thermoelectric cooler is activated, the temperature of the cold side 140 is reduced and thereby reduces the temperature of the adjacent conduit 412, which in turn reduces the temperature of refrigerant passing through the conduit 142. Further, the hot side 138 increases in temperature. The cooling source 148 supplies cold energy to the supplemental cooler 144 which thereby cools the adjacent hot side 138. By cooling the hot side 138, heat is removed from the housing 146 and the cooling efficiency of the supplemental cooler 144 is increased. It is further contemplated that the hot side 138 can be cooled by more conventional means such as moving air across it. Additionally, a heat sink can be provided in thermal communication with the hot side 138 to increase cooling efficiency.

Again referring to FIG. 3, one or more sensors may be disposed about the supply and exhaust lumens of the console 12 for detecting temperature, pressure, and/or flow rates through a particular portion of the console plumbing. For example, a first pressure sensor 150 may be disposed about the exhaust lumen 52 proximate to the umbilical connector. In addition, a second pressure sensor 152 may be disposed about the supply lumen 50. Additional sensors SS may be included throughout the console 12 for monitoring and/or controlling particular portions of the console and properties thereof.

In addition to the one or more sensors, one or more controllers may be coupled to the sensors, and in turn, coupled to one or more of the valves situated throughout the console 12 such that the valves may be controllably manipulated in response to information obtained by the sensors. For example, a first controller 154 may be coupled to the first pressure sensor 150, wherein the first controller 154 is further coupled to a valve 156 disposed on a portion of the exhaust line, and where the valve 156 may also be in fluid communication with the vacuum source 58. In addition, a second controller 158 may be coupled to the second pressure sensor 152, where the second controller 158 is further coupled to a valve 160 disposed about the supply lumen 50. Accordingly, fluid flow through portions of the exhaust and/or supply lumens may be controllably manipulated in direct response to the information obtained by sensors contained therein.

Figure 4:
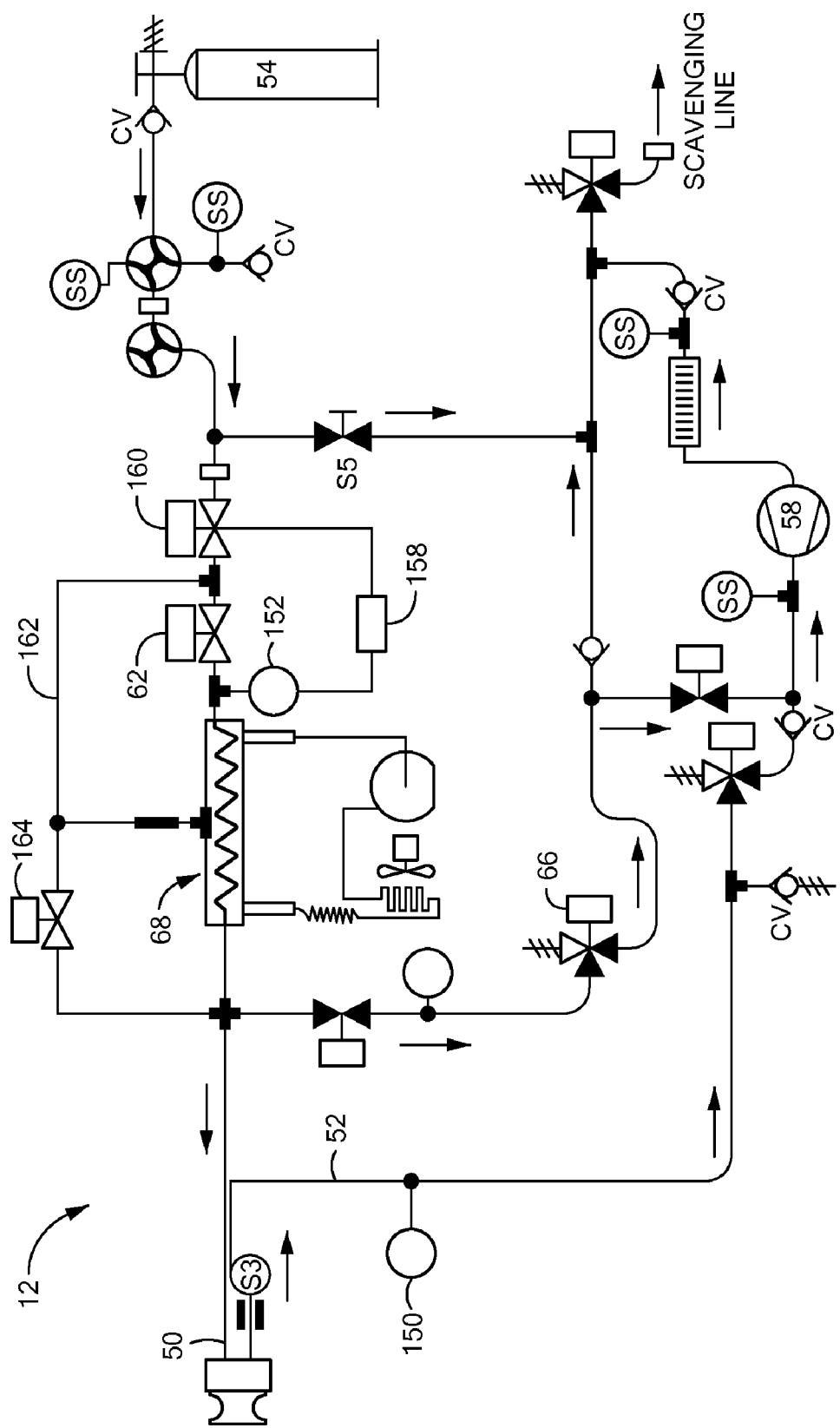
FIG. 4 is another schematic representation of an embodiment of a cooling system constructed in accordance with the principles of the present invention.

Now referring to FIG. 4, an embodiment of the console 12, such as a cooling system for a cryogenic medical device, is shown. As shown, the console contains several of the valves, sensors and components discussed above with respect to FIG. 3. The console 12 further includes a bypass coolant supply line 162 extending from a junction between valves 62 and 160. The bypass coolant supply line 162 includes a bypass valve 164, and rejoins the coolant supply line 50 on a distal side of the subcooler 68. The bypass coolant supply line 162 provides an avenue, conduit, or fluid pathway for delivery of coolant to the medical device without interacting or being exposed to the subcooler. The bypass may provide for the delivery of relatively warmer (or non-subcooled) coolant to the medical device 14 to inflate it without cooling, or to thaw or otherwise increase the temperature of a portion of the medical device 14, such as the treatment region 26.

In an exemplary use, the console 12 may be operated to deliver a refrigerant or coolant in a supercritical state to the medical device 14 for subsequent thermal treatment of selected tissue. A supercritical fluid is a substance at a temperature and pressure above its defined critical point. A critical point, also called a critical state, specifies the conditions (temperature, pressure and sometimes composition) at which a phase boundary ceases to exist. To reach or exceed a material's critical point, predetermined temperatures and pressure must be obtained. Critical properties vary from material to material, similar to melting points and boiling points.

Figure 11:
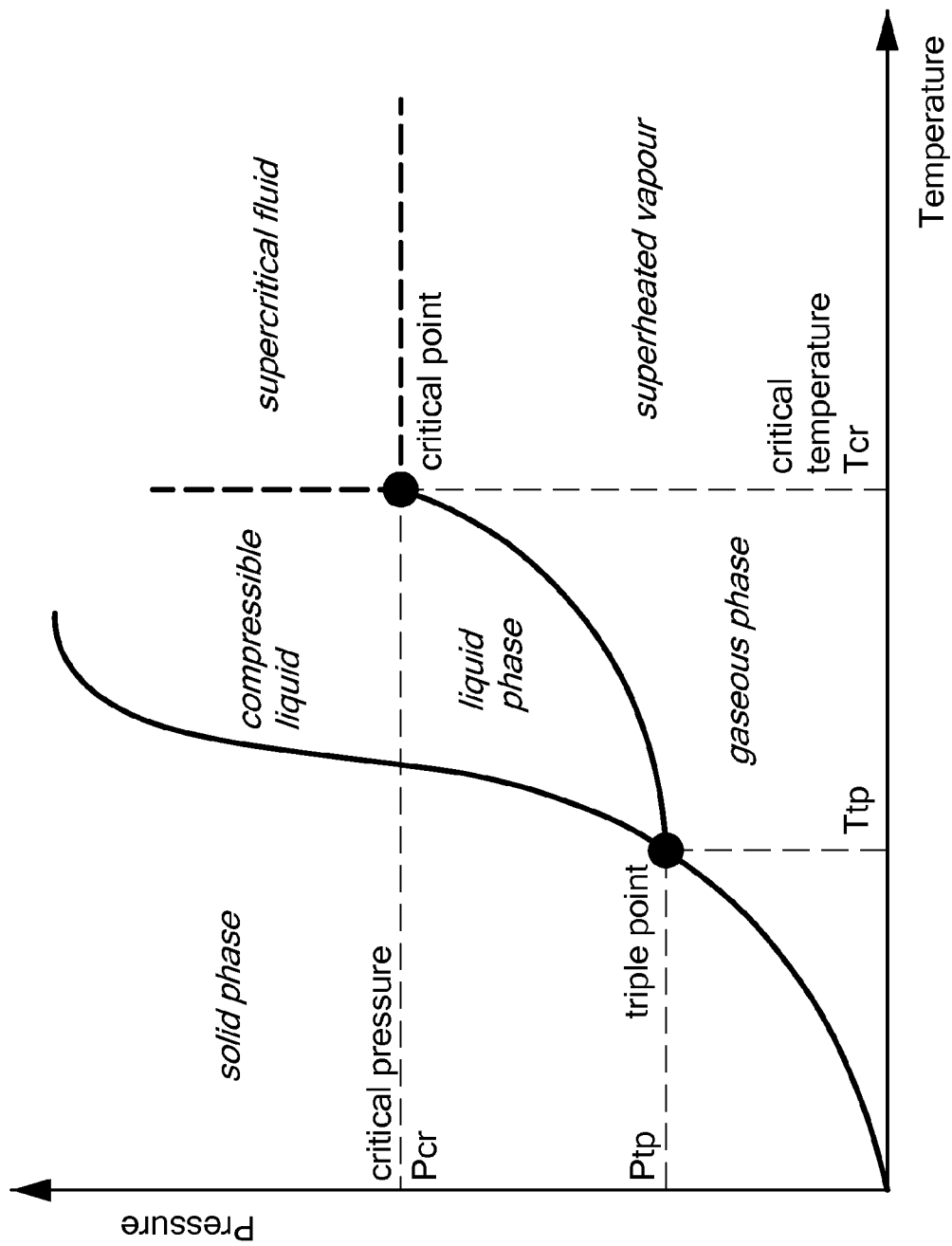
FIG. 11 is a diagram illustrating phase relationship to pressure and temperature.

As shown in the phase diagram of FIG. 11, the supercritical phase of a substance lies beyond the liquid and gaseous phases—resulting in a fluid having characteristics of both. Supercritical fluids typically have gaseous characteristics (such as the ability to diffuse through solids) as well as liquid characteristics (such as the ability to dissolve materials). In the pressure-temperature phase diagram of FIG. 11, boiling a material separates the gas and liquid region and ends in the critical point, where the liquid and gas phases disappear to become a single supercritical phase. As the critical temperature is approached, the density of the gas at equilibrium becomes denser, and that of the liquid lower. At the critical point, there is no difference in density, and the liquid and gaseous phases become one fluid phase. Thus, above the critical temperature a gas cannot be liquefied by pressure. A small increase in pressure causes a large increase in the density of the supercritical phase, allowing many properties of a supercritical fluid to be selectively and controllably manipulated. Many other physical properties also show large gradients with pressure near the critical point, e.g. viscosity, the relative permittivity and the solvent strength, which are all closely related to the density.

By delivering a supercritical fluid to the treatment region 26 of the medical device 14, lower temperatures can be achieved through the expansion and/or evaporation of the coolant once delivered to the treatment region. The lower temperatures may be obtained by using a Joule-Thompson valve to obtain the desired expansion. The supercritical coolant has increased thermodynamic capacity for cooling upon expansion compared to a liquid or gaseous phase, resulting in lower thermal temperatures—which reduces the time needed for tissue ablation.

In an exemplary method of operation, a coolant or refrigerant having a pre-defined critical point may be supplied by or otherwise contained in the first coolant reservoir 54. Exemplary coolants may include methane, argon, nitrogen, oxygen, krypton, and neon. The coolant in the first reservoir 54 may be at a pressure and/or temperature combination such that the coolant is in a liquid phase, or in a mixed liquid-gaseous phase. The first coolant reservoir 54 may include a dip tube or other structure to ensure that only the liquid-phase coolant is drawn from the reservoir 54 during use. The coolant may then proceed through the valves and conduits described above, which may direct the coolant through a subcooler prior to reaching the medical device 14. The subcooler may operate to modify the temperature and pressure characteristics of the coolant to ensure the supercritical state of the coolant passing through the supply lumen 50. Once passing through the subcooler, the remaining lengths of conduit leading to the treatment region 26 of the medical device may include insulative properties to reduce thermal exchange with the surrounding environment. To further increase the stability of the supercritical state of the coolant, the dimensions of the fluid supply tube leading to and through the length of the medical device 14 may be dimensioned to reduce the volume of coolant passing therethrough and to further maintain a desired pressure throughout the delivery path. Upon reaching the treatment region of the medical device 14, the supercritical coolant may be dispersed through a valve or expansion element, thereby allowing at least a portion of the ejected coolant to change phase into a liquid, gas and/or combination thereof. The expansion into a gaseous phase and subsequent evaporation of the liquid phase coolant within the treatment region 26 provides increased cooling capacity and reduced temperatures for thermal ablation of a selected tissue region.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A method of delivering coolant to a medical device, comprising:
    transferring a coolant in a supercritical state to a treatment region of the medical device; and
    changing the coolant from the supercritical state to at least one of a liquid phase and a gaseous phase at the treatment region.

2. The method of claim 1, wherein changing the coolant from the supercritical state to at least one of a liquid phase and a gaseous phase involves ejecting the coolant from a Joule-Thompson valve.

3. The method of claim 1, wherein the coolant is changed from a supercritical state into a mixed liquid-gaseous state.

4. The method of claim 1, wherein transferring the coolant in a supercritical state to a treatment region of the medical device includes subcooling the coolant.

5. The method of claim 1, further comprising
    drawing coolant from a reservoir in a liquid phase, and
    transitioning the coolant into a supercritical phase for delivery to the medical device.

6. The method of claim 1, wherein transitioning the coolant into a supercritical phase for delivery to the medical device includes raising the pressure of the coolant with a pressure regulator.

7. The method according to claim 1, further comprising monitoring a pressure level within the medical device.

8. The method according to claim 7, further comprising evacuating coolant from the medical device when the monitored pressure level varies from a predetermined target pressure.

9. The method according to claim 1, wherein the coolant is one of methane, argon, nitrogen, oxygen, krypton, and neon.

10. A method of cryogenically treating a tissue region, comprising:
    positioning a treatment region of a medical device proximate the tissue region;
    transferring coolant in a substantially liquid phase from a coolant reservoir to a subcooler;
    transitioning the coolant from the liquid phase into a supercritical state;
    transferring the supercritical coolant to the treatment region;
    changing the coolant from the supercritical state to at least one of a liquid phase and a gaseous phase at the treatment region;
    ablating the tissue region; and
    evacuating coolant from the treatment region of the medical device.

11. The method of claim 10, wherein changing the coolant from the supercritical state to at least one of a liquid phase and a gaseous phase involves ejecting the coolant from a Joule-Thompson valve.

12. The method according to claim 10, wherein the tissue region includes cardiac tissue.

13. The method according to claim 10, wherein the medical device is a catheter, and positioning a treatment region of the medical device proximate the tissue region includes routing at least a portion of the catheter through a blood vessel.

14. The method of claim 10, wherein the coolant is changed from a supercritical state into a mixed liquid-gaseous state at the treatment region.

15. The method according to claim 10, wherein the coolant is one of methane, argon, nitrogen, oxygen, krypton, and neon.

* * * * *